United States Patent
Kasahara et al.

[11] Patent Number: 6,054,605
[45] Date of Patent: Apr. 25, 2000

[54] 2, 3-DIHALOGENO-6-TRIFLUOROMETHYLBENZENE DERIVATIVES AND PROCESS FOR PRODUCING THE SAME

[75] Inventors: Isamu Kasahara; Tadashi Sugiura; Tsutomu Inoue, all of Kanagawa, Japan

[73] Assignee: Nippon Soda Co., Ltd., Tokyo, Japan

[21] Appl. No.: 09/249,076

[22] Filed: Feb. 12, 1999

Related U.S. Application Data

[62] Division of application No. 08/945,099, filed as application No. PCT/JP96/01688, Jun. 19, 1996.

[30] Foreign Application Priority Data

Jun. 20, 1995 [JP] Japan ................................ 7-176686
Aug. 10, 1995 [JP] Japan ................................ 7-225791
Aug. 25, 1995 [JP] Japan ................................ 7-242413
Jan. 18, 1996 [JP] Japan ................................ 8-24743

[51] Int. Cl.[7] .................................................. C07C 69/76
[52] U.S. Cl. ............................................. 560/103; 562/493
[58] Field of Search ............................ 562/493; 560/103

[56] References Cited

U.S. PATENT DOCUMENTS 5,502,235 3/1996 Zettler ...................................... 558/425

FOREIGN PATENT DOCUMENTS 2232154 5/1990 United Kingdom .

*Primary Examiner*—Joseph McKane
*Assistant Examiner*—Ebenezer Sackey
*Attorney, Agent, or Firm*—Jacobson, Price, Holman & Stern, PLLC

[57] ABSTRACT

The present invention is to provide 2,3-dihalogeno-6-trifluoromethylbenzene derivatives represented by a general formula [I];

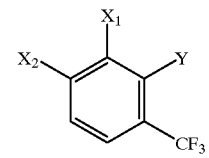

[I]

wherein $X_1$ and $X_2$ are the same or different and each independently represents fluoro or chloro; Y represents COOH, $CONH_2$, CN, CHO, CH=NOH or COOR', wherein R' is $C_1$–$C_4$ alkyl, except the case that $X_1$ and $X_2$ are each chloro and Y is COOH, which are useful as the starting materials for producing pesticides, drugs and the like, and a process for producing such derivatives.

4 Claims, No Drawings

2,3-DIHALOGENO-6-TRIFLUOROMETHYLBENZENE DERIVATIVES AND PROCESS FOR PRODUCING THE SAME

This application is a division of Ser. No. 08/945,099 filed on Dec. 22, 1997 which is a 371 of PCT/JP96/01688, filed Jun. 19, 1996.

FIELD OF THE INVENTION

The present invention is related to 2,3-dihalogeno-6-trifluoromethylbenzene derivatives useful as the starting material for producing pesticides, drugs and the like and a process for producing the said derivatives.

BACKGROUND ART

In connection with the present invention. 2,3-dichloro-6-trifluoromethylbenzoic acid, which is one of 2,3-dihalogeno-6-trifluoromethylbenzene derivatives, is disclosed in U.S. Pat. No. 3,823,134. In this disclosure, it is described that the compound can be synthesized as a mixture of 2,3-dichloro-5-trifluoromethylbenzoic acid and 4,5-dichloro-2-trifluoromethylbenzoic acid, however, the compound has not been isolated as a single substance and no physical data on the compound were recorded.

In the Japanese Patent Laid-open No. Hei 6-256257 Gazette, 2-trifluoromethyl-4,5,6-trifluorobenzoic acid and 2-trifluoromethyl-3,4,5,6-tetrafluorobenzoic acid are described as fluoro-trifluoromethylb enzoic acid derivatives. In addition, in the Japanese Patent Laid-open No. Hei 3-5436 Gazette, 2,3,4-trichloro-6-trifluoromethylbenzaldehyde, 2-trifluoromethyl-3-chloro-4,6-difluorobenzaldehyde and 2-trifluoromethyl-3,4,6-trifluorobenzaldehyde are described as nucleus-fluorinated trifluoromethylbenzaldehydes.

It is an object of the present invention to provide 2,3-dihalogeno-6-trifluoromethylbenzene derivatives useful as the starting material for producing pesticides, drugs, etc. and a process for producing the said derivatives.

DISCLOSURE OF THE INVENTION

The present invention is directed to 2,3-dihalogeno-6-trifluoromethylbenzoic acid, the derivatives thereof and a process for producing the same.

The present invention is described further in detail in the following.

(1) The present invention is directed to 2,3-dihalogeno-6-trifluoromethylbenzene derivatives represented by a general formula [I]:

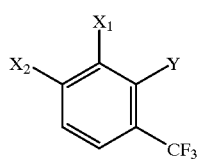

[I]

wherein $X_1$ and $X_2$ are the same or different and each independently fluoro or chloro, Y is a group selected from a group consisting of COOH, CONH2, CN, CHO, CH=NOH or COOR'. wherein R' is straight-chain or branched C1–C4 alkyl, such as methyl, ethyl, propyl, butyl, isopropyl and t-butyl, excluding the case wherein X1 and X2 are each chloro and Y is COOH.

As the definite examples for the 2,3-dihalogeno-6-trifluoromethyl be nzene derivatives described above, 2,3-dichloro-6-trifluoromethylbenzoic acid, 2,3-dichloro-6-trifluorometylbenzonitrile, 2,3-dichloro-6-trifluoromethylbenzamide, 2,3-dichloro-6-trifluoromethylbenzaldehyde, 2,3-dichloro-6-trifluoromethylbenzaldehyde oxime, methyl 2,3-dichloro-6-trifluoromethylbenzoate, ethyl 2,3-dichloro-6-trofluoromethylbenzoate, 3-chloro-2-fluoro-6-trifluoromethylbenzonitrile. 3-chloro-2-fluoro-6-trifluoromethylbenzamide, 3-chloro-2-fluoro-6-trifluoromethylbenzoic acid, 3-chloro-2-fluoro-6-trifluoromethybenzaldehyde, 3-chloro-2-fluoro-6-trifluoromethylbenzaldehyde oxime, methyl 3-chloro-2-fluoro-6-trifluoromethylbenzoate, ethyl 3-chloro-2-fluoro-6-trifluoromethylbenzoate, 2,3-difluoro-6-trifluoromethylbenzonitrile, 2,3-difluoro-6-trifluoromethylbenzamide, 2,3-difluoro-6-trifluoromethylbenzoic acid, 2,3-difluoro-6-trifluoromethylbenzaldehyde, 2,3-difluoro-6-trifluoromethylbenzaldehyde oxime, methyl 2,3-difluoro-6-trifluoromethylbenzoate, ethyl 2,3-difluoro-6-trifluoromethylbenzoate, 2-chloro-3-fluoro-6-trifluoromethylbenzonitrile, 2-chloro-3-fluoro-6-trifluoromethylbenzamide, 2-chloro-3-fluoro-6-trifluoromethylbenzoic acid, 2-chloro-3-fluoro-6-trifluoromethylbenzaldehyde, 2-chloro-3-fluoro-6-trifluoromethylbenzaldehyde oxime, methyl 2-chloro-3-fluoro-6-trifluoromethylbenzoate, ethyl 2-chloro-3-fluoro-6-trifluoromethylbenzoate, and the like can be given.

(2) The present invention is also directed to the following processes from (a) to (g).

(a) A process for producing a compound represented by a general formula (III);

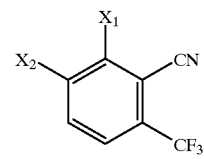

(III)

wherein $X_1$ and $X_2$ are as defined above, characterized in that the compound is obtained by allowing a compound represented by a general formula (II);

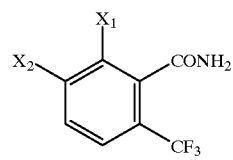

(II)

wherein $X_1$ and $X_2$ are as defined above, to react with a dehydrating agent.

(b) A process for producing a compound represented by a general formula (V);

(V)

wherein $X_2$ is as defined above, characterized in that the compound is obtained by allowing a compound represented by a general formula [IV];

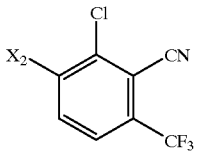

(IV)

wherein $X_2$ is as defined above, to react with a fluorinating agent.

(c) A process for producing 2,3-difluoro-6-trifluoromethylbenzonitrile, characterized in that the compound is obtained by allowing a compound represented by a general formula [VI];

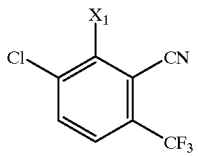

(VI)

wherein $X_1$ is as defined above, to react with a fluorinating agent.

(d) A process for producing 2-chloro-3-fluoro-6-trifluoromethylbenzonitrile, characterized in that the compound is obtained by firstly diazotizing the amino group in 2-amino-3-fluoro-6-trifluoromethylbenzonitrile with a diazotizing agent and subsequently allowing the said diazotized compound to react with a chlorinating agent.

(e) A process for producing 2-chloro-3-fluoro-6-trifluoromethylbenzonitrile, characterized in that the compound is obtained by allowing 2,3-difluoro-6-trifluoromethylbenzonitrile to react with a chloride compound.

(f) A process for producing 3-chloro-fluorobenzotrifluoride, characterized in that the compound is obtained by firstly causing the metallation of 4-chloro-3-fluorobenzotrifluoride with an organic metal and subsequently allowing the metallated compound to react with carbon dioxide.

(g) A process for producing 2,3-dichloro-6-trifluoromethylbenzoic acid, characterized in that the compound is obtained by firstly causing the metallation of 3,4-dichlorobenzotrifluoride with an organic metal and subsequently allowing the metallated compound to react with carbon dioxide.

Production of the compounds according to the present invention

The compounds according to the present invention can be produced according to the following production methods 1 through 10 as described below.

(Production Method 1)

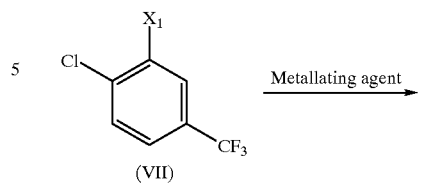

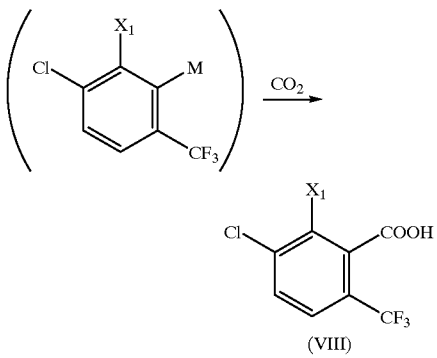

In the above-shown reaction formula for representing the production method 1, $X_1$ is as defined above, and M represents a metallic atom such as lithium.

This reaction is achieved by causing a metallation reaction of a compound represented by a general formula [VII] normally in a solvent at a temperature of from −80 to 0° C. more preferably at less than −50° C. by using a metallating agent, and then allowing the metallated product to react with carbon dioxide at a temperature of from −80 to 0° C. more preferably at less than −50° C. and subsequently to react with water at a temperature of from −10° C. to a room temperature. In this series of reactions, it is preferable to carry out the reactions up to the process of the reaction with carbon dioxide in water-free condition, and such reactions are normally conducted in the atmosphere using an inactive gas such as nitrogen gas. As the solvent usable in such reactions described above, ethers, such as tetrahydrofuran and diethyl ether, and a mixed solvent of any of such ethers and a hydrocarbon, such as pentane, hexane and cyclohexane, can be given. As the metallating agent, any of alkyl lithium compounds, such as n-butyl lithium, sec-butyl lithium, tert-butyl lithium and methyl lithium, can be used. It is also feasible to add a base, such as N,N,N',N'-tetramethyl ethylenediamine (TMEDA) and N,N,N',N',N'-pentamethyl diethylenetriamine (PMDTA), into the alkyl lithium compounds as described above, if appropriate. Furthermore, lithium diisopropylamide (LDA), potassium tert-butoxide, and the like can be used as the mutilating agent as described above.

(Production Method 2)

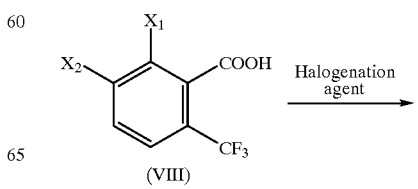

-continued

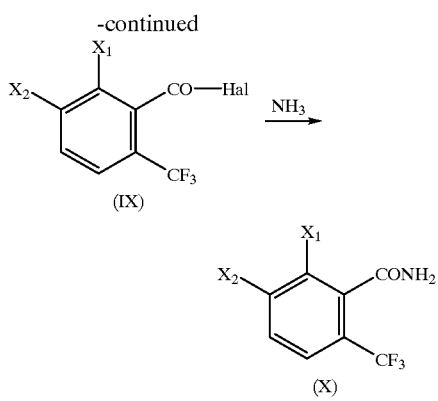

In the reaction formula illustrated above for representing the production method 2, $X_1$ and $X_2$ are as defined above and Hal represents a halogen atom.

The reaction above is achieved by converting a compound represented by a general formula [VIII] to an acyl halide by using a halogenating agent and subsequently allowing the acyl halide obtained to react with ammonia.

The reaction to convert the compound of the formula [VIII] to an acyl halide with a halogenating agent is normally carried out by using a halogenating agent in a solvent at a temperature ranging from a room temperature to the boiling point of the solvent. For the acceleration of the reaction, a base, such as pyridine and triethylamine, may be used in the reaction. As the halogenating agent, thionyl chloride, phosphorus trichloride, phosphorus pentachloride, phosphorus oxychloride, oxalyl chloride, phosgene, and the like can be used in the reaction. As the employable solvents in this reaction, aromatic hydrocarbons, such as benzene, toluene and xylene, halogenated hydrocarbons, such as chloroform and ethylene dichloride, and the mixtures of such hydrocarbons, can be given, though a halogenating agent can be additionally used as the solvent for this reaction.

The process to allow the acyl halide to react with ammonia can be achieved according to a method to gradually add the acyl halide into aqueous ammonia maintained at a temperature of from −5 to 10° C. and then to stir the mixture at room temperature or a method to gradually add the acyl halide into aqueous ammonia diluted with ethanol and maintained at a temperature of from 0 to 15° C. and then to stir the mixture at a room temperature, for example.

(Production Method 3)

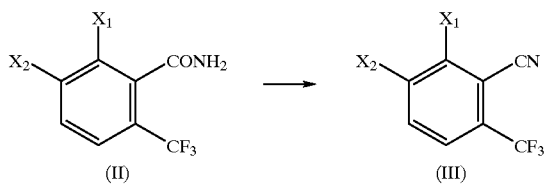

In the reaction formula illustrated above for representing the production method 3, $X_1$ and $X_2$ are as defined above.

The reaction is initiated by the application of a dehydrating agent either in or without the presence of a solvent at a temperature ranging from 0° C. to the boiling point of the solvent used. The dehydrating agent is defined here as a reacting agent for converting a benzamide to a benzonitrile. As the example for such a dehydrating agent, phosphorus oxychloride, thionyl chloride, phosphorus pentachloride, N,N'-dicyclohexylcarbodimide (DCC), trifluoroacetic anhydride, acetic anhydride, chloroethylformate, chloromethylformate, paratoluene sulfonyl chloride, methane sulfonyl chloride, and the like can be given. As the example for the solvent usable in the reaction, aromatic hydrocarbons, such as benzene, toluene and xylene, halogenated hydrocarbons, such as chloroform and ethylene dichloride, ethers, such as tetrahydrofuran (THF) and dioxane, pyridine and the mixtures thereof can be given. though a halogenating agent can be additionally used as the solvent for this reaction. Further, a base such as triethyl amine may be added into the solvent, if required.

(Production Method 4)

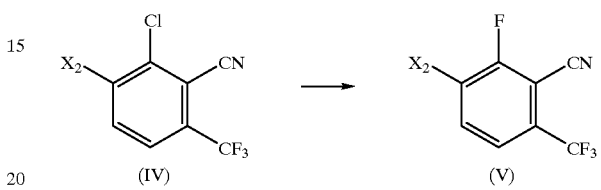

In the reaction formula illustrated above for representing the production method 4, $X_1$ and $X_2$ are as defined above.

The reaction is achieved by applying a fluorinating agent normally in a solvent at a temperature of from 60 to 200° C., more preferably from 90 to 180° C., in the atmosphere using an inactive gas such as nitrogen gas, if appropriate. As the example for the solvent used for the reaction, aromatic hydrocarbons, such as benzene, toluene and xylene, aprotic polar solvents, such as N,N-dimethylformamide, dimethylsulfoxide and sulfolane, and the mixtures thereof can be given. Whereas, as the example for the fluorinating agent, potassium fluoride, cesium fluoride, tetramethylammonium fluoride, and the like can be given. Whereas, as the example for a catalyst for the reaction, ethers, such as 18-crown-6 and dicyclohexyl-18-crown-6, quaternary ammonium salts, such as tetrabutylammonium bromide, tetrabutylammonium chloride, methyltrioctylammonium chloride and benzyltriethylammonium chloride, phosphonium compounds, such as tetraphenylphosphonium bromide and hexadecyltributylphosphonium iodide, can be given.

(Production Method 5)

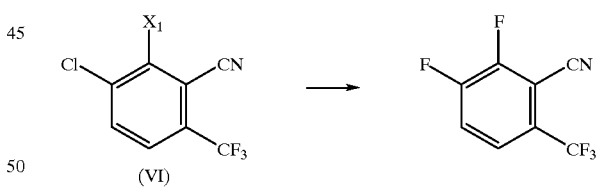

In the reaction formula illustrated above for representing the production method 5, $X_1$ is as defined above.

The reaction is achieved by applying a fluorinating agent normally in a solvent at a temperature of from 100 to 250° C. more preferably from 150 to 200° C. in the atmosphere using an inactive gas such as nitrogen gas, if appropriate. As the example for the solvent used for the reaction, aromatic hydrocarbons, such as toluene and xylene, aprotic polar solvents, such as N,N-dimethylformamide, dimethylsulfoxide and sulfolane, and the mixtures thereof can be given. Whereas, as the example for the fluorinating agent, potassium fluoride, cesium fluoride, tetramethylammonium fluoride, and the like can be given. Whereas, as the example for a catalyst for the reaction, ethers, such as 18-crown-6 and dicyclohexyl-18-crown-6, quaternary ammonium salts, such as tetrabutylammonium bromide, tetrabutylammonium chloride, methyltrioctylammonium chloride and benzyltriethylammonium chloride, phosphonium compounds, such as tetraphenylphosphonium bromide and hexadecyltributylphosphonium iodide, can be given.

(Production Method 6)

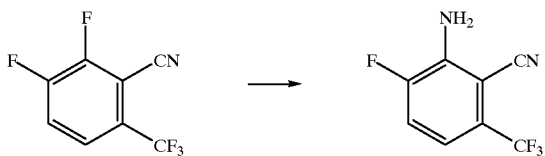

In the reaction formula illustrated above for representing the production method 6, $X_1$ is as defined above.

The reaction is achieved by applying an aminating agent normally in a solvent at a temperature of from 0 to 150° C., more preferably from 40 to 80° C. As the example for the solvent used for this reaction, aromatic hydrocarbons, such as benzene, toluene and xylene, aprotic polar solvents, such as N,N-dimethylformamide, dimethylsulfoxide and sulfolane, alcohols, such as ethanol and methanol, water and the mixtures thereof can be given. Whereas, as the example for the aminating agent, ammonium carbonate, aqueous ammonia, ammonia-containing ethanol and the like can be given.

(Production Method 7)

The reaction is achieved by applying a diazotizing agent such as sodium nitrite normally in an aqueous solution of hydrochloric acid, sulfuric acid or the like at a temperature of from −20 to 50° C. more preferably from −5 to 10° C. to prepare a diazonium salt and subsequently adding the solution of the diazonium salt gradually into either aqueous solution or hydrochloric acid solution of copper(I) chloride at a temperature of from 0 to 100° C. more preferably from 15 to 60° C. Alternatively, the reaction is also achieved by suspending anhydrous copper(II) chloride as a chlorinating agent into a solvent such as acetonitrile or the like, adding an alkyl nitrite as a diazotizing agent, such as tert-butyl nitrite and isopentyl nitrite, and subsequently adding 2-amino-3-fluoro-6-trifluoromethylbenzonitrile into the solution at a temperature of from −10 to 15° C. and further allowing the solution to the reaction at room temperature.

(Production Method 8)

The reaction is achieved by applying a chloride compound normally in an inactive solvent at a temperature of from 50 to 250° C. sore preferably from 100 to 200° C. As the example for the solvent used for the reaction, aprotic polar solvents, such as dimethylsulfoxide (DMSO), sulfolane, N,N-dimethylformamide (DMF) and 1,3-dimethyl-2-imidazolidinone, aromatic hydrocarbons, such as dichlorobenzene and trichlorobenzene, and the mixtures thereof can be given. Whereas, as the example for the chloride compound described above, alkali metal chlorides and alkaline earth metal chlorides, such as calcium chloride, lithium chloride, sodium chloride and potassium chloride, can be given.

(Production Method 9)

The compounds according to the present invention can be also produced according to the following reaction formula.

(Production Method 10)

Benzoate compounds as the compound according to the present invention can be obtained by allowing the corresponding benzoic acid to react with an alcohol in the presence of an acid catalyst, or by allowing the corresponding benzoyl chloride to react with either of an alcohol or an alkoxide preferably in the presence of a base.

When either of such methods were employed, the objective product can be obtained after taking normal procedure for the post-treatment of the reaction product.

The chemical structures of the compounds according to the present invention were determined based on the data obtained by using IR, NMR, Mass, and other available means.

BEST MODE FOR CARRYING OUT THE INVENTION

EXAMPLES

The present invention is further described in detail with referring the following examples.

Example 1

2,3-dichloro-6-trifluoromethylbenzoic acid
(Compound No. 11)

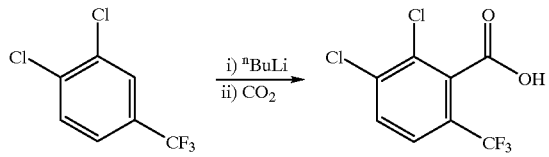

83.4 g of 3,4-dichlorobenzotrifluoride was dissolved in 800 ml of dried tetrahydrofuran, and 250 ml of hexane solution of n-butyl lithium(1.6 mol/l) was added to the solution dropwise over 15 minutes at −78° C. under nitrogen atmosphere. Following to stirring the solution for 2 hours at −78° C., 50 g of dry ice was then gradually added to the solution at the same temperature. After elevating the temperature of the solution up to room temperature, 250 ml of cold water was added to the solution to separate the resulting solution, and the aqueous layer obtained was adjusted to an acidic condition of a pH value of 1 with concentrated hydrochloric acid while cooling. Then, the aqueous layer was extracted with ether, and the extract was washed with water and dried over anhydrous magnesium sulfate. The solvent was distilled out under reduced pressure, and the oily residue obtained was crystalized with n-hexane, washed, filtered, and dried to obtain 89 g of the title compound(mp. 88–89° C.).

Example 2

2,3-dichloro-6-trifluoromethylbenzamide
(Compound No. 21)

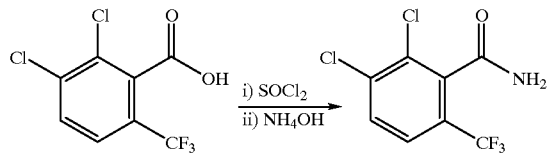

To a solution of 250 g of 2,3-dichloro-6-trifluoromethylbenzoic acid in 2 liters of benzene was added 5 drops of pyridine and 172 g of thionyl chloride and then the mixture was heated at reflux for 22 hours. After cooling down, the solution was concentrated under reduced pressure, and 2,3-dichloro-6-trifluoromethylbenzyl chloride obtained was added into 1 liter of 28% aqueous ammonia solution, which has been cooled down to 5° C. over 10 minutes with stirring. Then, the solution was further stirred for 1 hour at room temperature. The reaction mixture was extracted with ethyl acetate, and the extract was washed with water and then with saturated saline solution, and was dried over anhydrous magnesium sulfate. The solvent was distilled under reduced pressure, and the crude crystals obtained were washed with n-hexane and then filtered to give 229 g of the title compound(mp. 118–20° C.).

Example 3

2,3-dichloro-6-trifluoromethylbenzonitrile
(Compound No. 31)

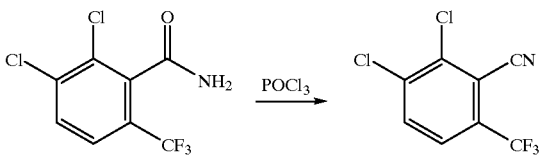

To a solution of 229 g of 2,3-dichloro-6-trifluoromethylbenzamide in 2 liters of benzene was added 409 g of phosphorus oxychloride and then the mixture was heated at ref lux for 3.5 hours. After cooling, the solution was gradually added into 2 liters of water maintained at 30–40° C. to hydrolyze the excess phosphorus oxychloride therein and was allowed to separation. The aqueous layer was extracted with benzene, and the extract was combined with the organic layer previously obtained, washed with water and with saturated saline solution and dried over anhydrous magnesium sulfate. The solvent was distilled under reduced pressure, and the crude product obtained was washed with n-hexane and filtered to obtain 204 g of the title compound(mp. 53–54° C.).

Example 4

2,3-dichloro-6-trifluoromethylbenzonitrile
(Compound No. 31)

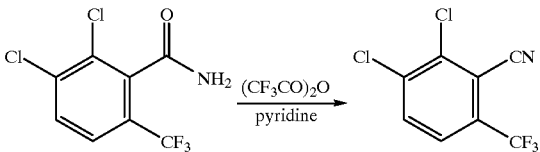

409 g of 2,3-dichloro-6-trifluoromethylbenzamide was dissolved in 2 liters of dioxane, and 263 g of pyridine was further added to the resultant solution. To this solution, 349 g of trifluoroacetic anhydride was added dropwise over 30 minutes while maintaining the temperature from 7 to 10° C. After stirring the solution for 2 hours at 25° C., the reaction mixture was poured into ice water. The precipitated crystals generated were then collected by filtration and were dissolved in ethyl acetate. The solution was then washed with water and saturated saline solution in series and dried over anhydrous magnesium sulfate. The solvent was distilled under reduced pressure, and the crude product obtained was washed with n-hexane and filtered to obtain 358 g of the title compound(mp. 53–54° C.).

Example 5

3-chloro-2-fluoro-6-trifluoromethylbenzoic acid
(Compound No. 12)

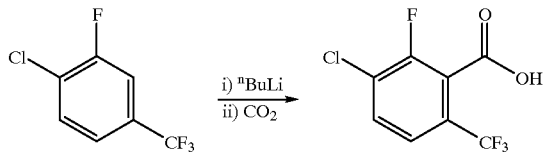

77.0 g of 3-fluoro-4-chlorobenzotrifluoride was dissolved in 750 ml of dried tetrahydrofuran, and to the solution, 250 ml of hexane solution of n-butyl lithium (1.6 mol/l) was added dropwise over 15 minutes at −78° C. under a nitrogen atmosphere. After stirring the solution at −78° C. for 2 hours. 50 g of dry ice was gradually added to the solution at the same temperature. After elevating the temperature of the solution up to room temperature, 500 ml of ice water was added to the solution to separate the resulting solution. While cooling down the aqueous layer, the layer was adjusted to a pH value of 1 with concentrated hydrochloric acid. The aqueous layer was then extracted with ether, washed with water and dried over anhydrous magnesium sulfate. The solvent was distilled under reduced pressure, and the oily residue obtained was crystalized with n-hexane, followed by a filtration and then dried to obtain 88.4 g of the title compound(mp. 92–93° C.).

Example 6

3-chloro-2-fluoro-6-trifluoromethylbenzamide
(Compound No. 22)

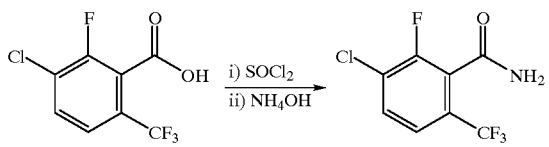

420 g of thionyl chloride was added to 286 g of 3-chloro-2-fluoro-6-trifluoromethylbenzoic acid, and to the resultant mixture was further added 5 drops of triethylamine and the mixture then heated at reflux for 4 hours. After cooling, the reaction mixture was concentrated under reduced pressure, and 3-chloro-2-fluoro-6-trifluoromethylbenzoyl chloride obtained was added into 1 liter of 28% aqueous ammonia solution, which has be cooled down to 5° C. over 10 minutes with stirring. Then. the solution was further stirred for 1 hour at room temperature. The reaction mixture was extracted with ether, and the extract was washed with water and with saturated saline solution and dried over anhydrous magnesium sulfate. The solvent was distilled under reduced pressure, and the crude crystals obtained were washed with n-hexane and then filtered to obtain 266 g of the title compound(mp. 123–125° C.).

Example 7

3-chloro-2-fluoro-6-trifluoromethylbenzonitrile
(Compound No. 32)

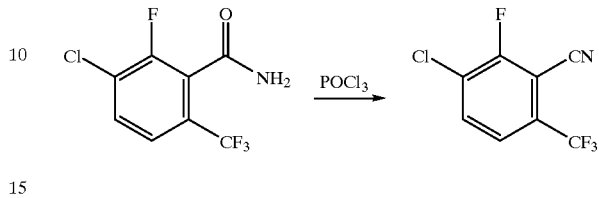

To a solution of 266 g of 3-chloro-2-fluoro-6-trifluoromethylbenzamide in 2.5 liters of 1,2-dichloroethane was added 339 g of phosphorus oxychloride and then the mixture was heated at reflux for 18.5 hours. After cooling, the solution was gradually added into 2 liters of water maintained at 30–40° C. to hydrolyze the excess amount of phosphorus oxychloride and was then separated. The aqueous layer was extracted with chloroform, and the extract was combined with the organic layer previously obtained, washed with IN aqueous solution of sodium hydroxide, water and saturated saline solution in series, and then dried over anhydrous magnesium sulfate. The solvent was distilled under reduced pressure, and the crude product obtained was washed with chilled n-hexane and then filtered to obtain 228 g of the title compound(mp. 43–44° C.).

Example 8

3-chloro-2-fluoro-6-trifluoromethylbenzonitrile
(Compound No. 32)

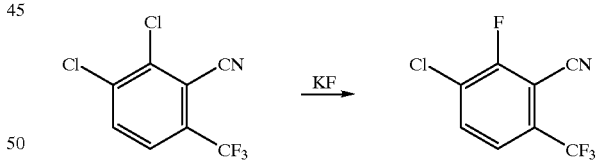

To a solution of 0.96 g of 2,3-dichloro-6-trifluoromethylbenzonitrile in 7 ml of N,N-dimethylformamide was added 0.46 g of spray-dried potassium fluoride and 0.1 g of 18-crown-6-ether and the mixture was stirred for 6 hours at 100° C. under a nitrogen atmosphere. After cooling, the reaction mixture was poured into ice water and extracted with ethyl acetate. The organic layer was washed with saturated saline solution and dried over anhydrous magnesium sulfate. After distilling the solvent under reduced pressure, the crude product obtained was purified by using silica gel column chromatography to obtain 0.65 g of the title compound(mp. 43–44° C.).

Example 9

2,3-difluoro-6-trifluoromethylbenzonitrile
(Compound No. 34)

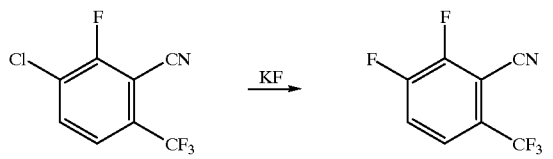

To a solution of 35.0 g of 3-chloro-2-fluoro-6-trifluoromethylbenzo nitrile in 200 ml of sulfolane was added 36.3 g of spray-dried potassium fluoride and 4.1 g of 18-crown-6-ether, and the mixture was stirred for 7 hours at 160–170° C. under a nitrogen atmosphere. After cooling, the reaction mixture was poured into ice water and extracted with ethyl acetate. The organic layer obtained was washed with saturated saline solution and then dried over anhydrous magnesium sulfate. Following to the concentration of the extract, the oily product obtained was distilled under reduced pressure to obtain 25.7 g of the title compound (bp. 98–100° C. (25 mmHg) nD 20.0-1.4413).

Example 10

2,3-difluoro-6-trifluoromethylbenzonitrile
(Compound No. 34)

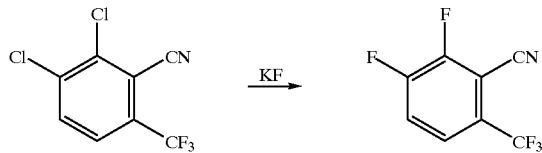

To a solution of 41.8 g of 2,3-dichloro-6-trifluoromethylbenzonitrile in 250 ml of sulfolane was added 40.4 g of spray-dried potassium fluoride and 4.6 g of 18-crown-6-ether, and the mixture was stirred for 20 hours at 160–170° C. under a nitrogen atmosphere. After cooling, the reaction mixture was poured into ice water and extracted with ethyl acetate. The organic layer obtained was washed with saturated saline solution and then dried over anhydrous magnesium sulfate. After conducting the concentration of the extract, the oily product obtained was distilled under reduced pressure to obtain 27.5 g of the title compound (bp. 98–100° C. (25 mmHg)).

Reference Example 1

2-amino-3-fluoro-6-trifluoromethylbenzonitrile

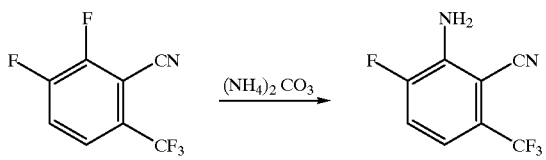

To a solution of 25.7 g of 2,3-difluoro-6-trifluorobenzonitrile in 200 ml of dimethyl sulfoxide (DMSO) was added 14.5 g of ammonium carbonate and the mixture was stirred for 2 hours at 100° C. After cooling, the reaction mixture was added with water and then extracted with ether. The organic layer obtained was washed with saturated saline solution and then dried over anhydrous magnesium sulfate. After conducting the concentration of the extract, the crude product obtained was purified by using silica gel column chromatography to obtain 18.5 g of the title compound (mp. 100.5–102° C.).

Example 11

2-chloro-3-fluoro-6-trifluoromethylbenzonitrile
(Compound No. 33)

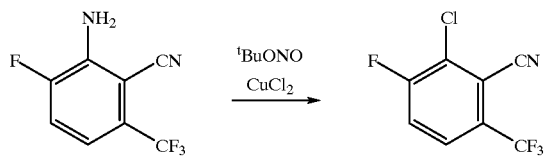

14.6 g of anhydrous copper(II) chloride was suspended in 250 ml of acetonitrile, and to the resultant mixture was further added 14.0 g of t-butyl nitrite at 0~5° C. After stirring for 10 minutes, to the reaction mixture, a solution of 18.5 g of 2-amino-3-fluoro-6-trifluoromethylbenzonitrile in 80 ml acetonitrile was added dropwise over 10 minutes at 0~5° C. The solution was then stirred for 1 hour at a temperature of from 0 to 5° C. and further for 4 hours at room temperature. The reaction mixture was then added with water and extracted with ether. The organic layer obtained was washed with diluted hydrochloric acid and subsequently with water and dried over anhydrous magnesium sulfate. After concentrating the organic layer, the oily product obtained was purified by using silica gel column chromatography to obtain 16.2 g of the title compound [bp. 104–107° C.(15 mmHg). nD 20.7-1.4660].

Example 12

2-chloro-3-fluoro-6-trifluoromethylbenzonitrile
(Compound No. 33)

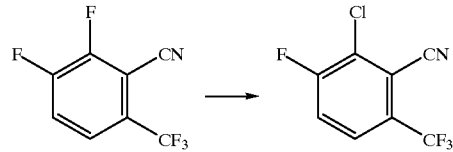

To a solution of 50.9 g of 2,3-difluoro-6-trifluoromethylbenzonitrile in 240 ml of dimethyl sulfoxide (DMSO) was added 53.3 g of calcium chloride and the mixture was stirred for 6 hours at a temperature of from 140 to 150° C. After cooling, the reaction mixture was further added with 240 ml water and extracted with 240 ml and 100 ml hexane twice. The organic layer obtained was dried over anhydrous magnesium sulfate, and the solvent therein was distilled under reduced pressure. The crude product obtained was distilled under reduced pressure to obtain 38.9 g of the title compound.

Example 13

2,3-difluoro-6-trifluoromethylbenzaldehyde
(Compound No. 44)

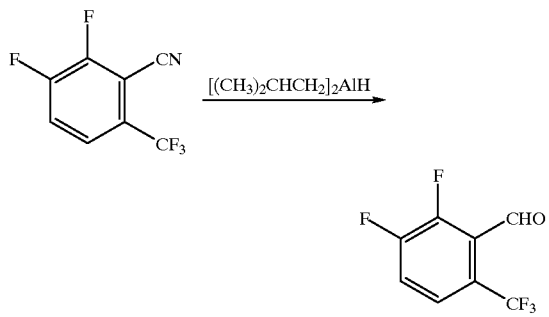

2.0 g of 2,3-difluoro-6-trifluoromethylbenzonitrile was dissolved in 20 ml of anhydrous dichloromethane and the resultant solution was cooled down to −78° C. under a nitrogen atmosphere. To the solution was then gradually added dropwise with 7.1 ml of 1.5 M toluene solution of diisobutyl aluminium hydride (DIBAL) over 30 minutes. After stirring the solution at −78° C. for 1 hour, the solution was allowed to room temperature. The solution was then added with 7 ml of saturated aqueous solution of ammonium chloride, stirred for 30 minutes and subsequently added with 33 ml of 5% sulfuric acid. The mixture was then extracted with ether, and the organic layer obtained was washed with saturated saline solution and was then dried over anhydrous magnesium sulfate. After a process for the concentration, the organic solution was purified by using silica gel column chromatography to obtain 1.36 g of the title compound (nD 20.6-1.4357).

The aldehyde compound obtained here was easily oxidized if it is left in the air and was converted to the corresponding benzoic acid (Compound No. 14).

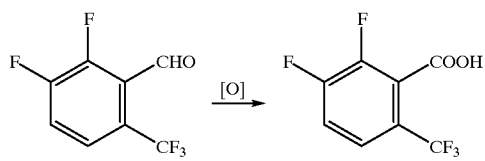

Example 14

2,3-difluoro-6-trifluoromethylbenzaldehyde oxime
(Compound No. 54)

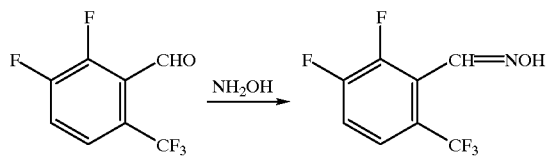

To a solution of 0.5 g of 2,3-difluoro-6-trifluoromethylbenzaldehyde in 8 ml of ethanol was added 0.4 g of hydroxylamine hydrochloride and a solution prepared by dissolving 0.23 g of sodium hydroxide into 2 ml of water and the mixture was heated at reflux for 40 minutes. The reaction mixture was allowed to room temperature, then concentrated under reduced pressure and extracted with ethyl acetate. The extract obtained was washed with water and with saturated saline solution and dried over anhydrous magnesium sulfate. After concentrating the extract solution, the crude product obtained was washed with n-hexane to obtain 0.24 g of the title compound (mp. 111–112° C.).

Example 15

Methyl 2,3-dichloro-6-trifluoromethylbenzoate
(Compound No. 55)

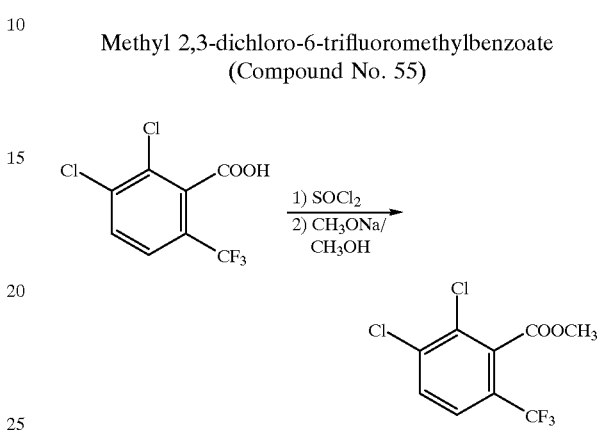

To a solution of 1.04 g of 2,3-dichloro-6-trifluoromethylbenzoic acid in 10 ml of toluene was added 0.71 g of thionyl chloride and 1 drop of pyridine and the mixture was heated at reflux for 3 hours. After cooling, the reaction mixture was concentrated under reduced pressure, and 2,3-dichloro-6-trifluoromethylbenzoyl chloride obtained was added to a solution which is prepared by dissolving 28% methanol solution of 0.77 g of sodium methoxide into 10 ml of methanol at a temperature of from 5 to 10° C., and the solution was stirred for 2 hours at room temperature. After condensing the reaction mixture, it was extracted with ether. The extract was washed with 1N-aqueous hydrochloric acid, water and saturated saline solution in series and then dried over anhydrous magnesium sulfate. The solvent was distilled under reduced pressure, and the oily substance obtained was purified by using silica gel column chromatography to obtain 0.89 g of the title compound (nD 23.3-1.4801).

The representative examples for the compounds according to the present invention including the ones disclosed in the examples described above are shown in Tables 1 through 6.

TABLE 1

| Compound No. | $X_1$ | $X_2$ | Physical Constant (Melting point) |
|---|---|---|---|
| 11 | Cl | Cl | 88–89° C. |
| 12 | F | Cl | 92–93° C. |
| 13 | Cl | F | 111–112° C. |
| 14 | F | F | 90–92° C. |

TABLE 2

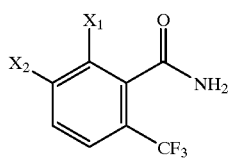

| Compound No. | $X_1$ | $X_2$ | Physical Constant (Melting point) |
|---|---|---|---|
| 21 | Cl | Cl | 118–120° C. |
| 22 | F | Cl | 123–125° C. |
| 23 | Cl | F | 103–105° C. |
| 24 | F | F | 108–110° C. |

TABLE 3

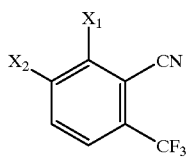

| Compound No. | $X_1$ | $X_2$ | Physical Constant (Melting point or Boiling point) |
|---|---|---|---|
| 31 | Cl | Cl | 53–54° C. |
| 32 | F | Cl | 43–44° C. |
| 33 | Cl | F | bp 104–107° C. (15 mmHg) |
| 34 | F | F | bp 98–100° C. (25 mmHg) |

TABLE 4

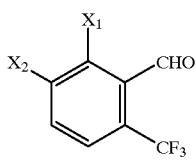

| Compound No. | $X_1$ | $X_2$ | Physical Constant (Refractive Index) |
|---|---|---|---|
| 41 | Cl | Cl | $n_D^{20.4}$ 1.4955 |
| 42 | F | Cl | $n_D^{21.1}$ 1.4726 |
| 43 | Cl | F | $n_D^{18.7}$ 1.4673 |
| 44 | F | F | $n^{20.6}$ 1.4357 |

TABLE 5

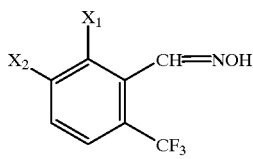

| Compound No. | $X_1$ | $X_2$ | Physical Constant (Melting point) |
|---|---|---|---|
| 51 | Cl | Cl | 102–104° C. |
| 52 | F | Cl | 119–120° C. |
| 53 | Cl | F | 56–57° C. |
| 54 | F | F | 111–112° C. |

TABLE 6

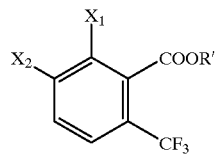

| Compound No. | $X_1$ | $X_2$ | R' | Physical Content (Refractive Index) |
|---|---|---|---|---|
| 55 | Cl | Cl | $CH_3$ | $n_D^{23.3}$ 1.4801 |
| 56 | Cl | Cl | $C_2H_5$ | $n_D^{24.1}$ 1.4748 |
| 57 | Cl | Cl | $C_3H_7$ | |
| 58 | Cl | Cl | i-$C_3H_7$ | |
| 59 | Cl | Cl | t-$C_4H_9$ | |
| 60 | F | Cl | $CH_3$ | |
| 61 | F | Cl | $C_2H_5$ | |
| 62 | Cl | F | $CH_3$ | |
| 63 | Cl | F | $C_2H_5$ | |
| 64 | F | F | $CH_3$ | |
| 65 | F | F | $C_2H_5$ | |

INDUSTRIAL USE 2,3-dihalogeno-6-trifluoromethylbenzene derivatives according to the present invention are useful as the starting materials for producing pesticides, drugs and the like. For example, the compounds according to the present invention can be used as the starting material for producing a fungicide for agricultural and horticultural use containing benzamidoxime derivatives described in Japanese Application No. 6-334497 corresponding to WO 96/19442. Moreover, according to the production process specified in the present invention, the production of such compounds in an industrial scale can be achieved advantageously.

What is claimed is:

1. 2,3-dihalogeno-6-trifluoromethylbenzene derivatives represented by a general formula [I];

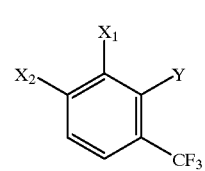

wherein $X_1$ and $X_2$ are the same or different and each independently represent fluoro or chloro and Y is COOH or COOR', wherein R' is straight-chain or branched $C_1$–$C_4$ alkyl, except the case that $X_1$ and $X_2$ are each chloro, and Y is COOH.

2. 3-chloro-2-fluoro-6-trifluoromethylbenzoic acid.

3. A process for producing 3-chloro-2-fluoro-6-trifluoromethylbenzoic acid, wherein the compound is prepared by reacting 4-chloro-3-fluorobenzotrifluoride to a with an organic metal and subsequently adding solid carbon dioxide to the metallated compound.

4. A process for producing 2,3-dichloro-6-trifluoromethylbenzoic acid, wherein the compound is prepared by reacting 3,4-dichlorobenzotrifluoride to a metallation with an organic metal and then adding solid carbon dioxide to the compound.

* * * * *

UNITED STATES PATENT AND TRADEMARK OFFICE
CERTIFICATE OF CORRECTION

PATENT NO. : 6,054,605
DATED : April 25, 2000
INVENTOR(S) : Isamu KASAHARA et al It is certified that error appears in the above-identified patent and that said Letters Patent is hereby corrected as shown below:

Column 18, line 59, --metallation-- is inserted before "with".

Signed and Sealed this

Tenth Day of April, 2001

Attest:

NICHOLAS P. GODICI

*Attesting Officer*    Acting Director of the United States Patent and Trademark Office